Figure 1:
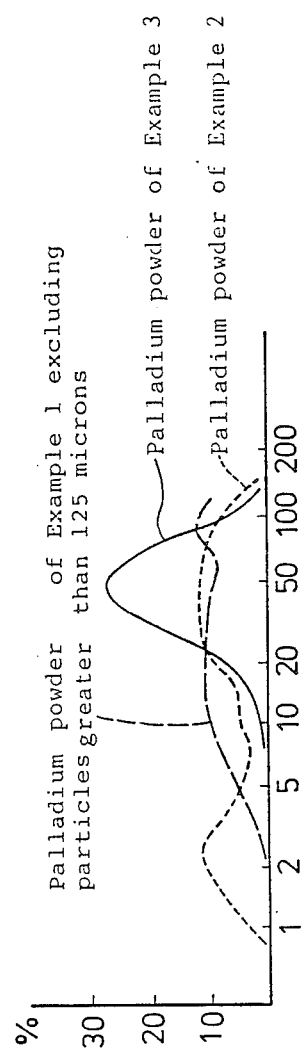

United States Patent [19]

Wey

[11] Patent Number: 4,711,743

[45] Date of Patent: Dec. 8, 1987

[54] PROCESS FOR PRODUCING ANTHRAQUINONE-1-SULPHONIC ACID BY SULPHONATION WITH PALLADIUM CATALYST

[75] Inventor: Feng-Feng Wey, Hsinchu, Taiwan

[73] Assignee: 501 China Technical Consultants, Inc., Taipei, Taiwan

[21] Appl. No.: 5,996

[22] Filed: Jan. 21, 1987

[51] Int. Cl.$^4$ ............................................. C07C 143/36
[52] U.S. Cl. .................................... 260/370; 502/201; 502/339
[58] Field of Search ................. 260/370; 502/201, 339

[56] References Cited

U.S. PATENT DOCUMENTS 3,763,191  10/1973  Schmitz et al. ..................... 260/370

*Primary Examiner*—Glennon H. Hollrah
*Assistant Examiner*—Raymond K. Covington
*Attorney, Agent, or Firm*—Townsend & Townsend

[57] ABSTRACT

A process for the production of anthraquinone-1-sulphonic acid by sulphonating anthraquinone with a sulphonating agent in the presence of palladium catalyst in a solvent, is characterized in that before sulphonation, the palladium is mixed with nitric acid or mineral acids containing nitric acid at room temperature and then the acid is removed from the treated palladium. Preferably, the sulphonating agent of 1–10% $SO_3$ is first mixed with the nitric acid treated palladium as a solvent, and the same sulphonating agent of 50–65% $SO_3$ is added for sulphonation at about 90–100 degs. C.

9 Claims, 1 Drawing Figure

PROCESS FOR PRODUCING ANTHRAQUINONE-1-SULPHONIC ACID BY SULPHONATION WITH PALLADIUM CATALYST

BACKGROUND OF THE INVENTION

This invention relates to a process for the production of anthraquinone-1-sulphonic acid by sulphonating anthraquinone in the presence of a palladium catalyst, and particularly to a process characterized in that the palladium catalyst is treated with nitric acid or other acids containing nitric acid.

Processes for the production of anthraquinone sulphonic acids are known in the art. German Pat. No. 149,801 discloses a process in which anthraquinone is sulphonated in $SO_3$ containing sulphuric acid in the presence of mercury, mercury salts or thallium salts. However, the sulphonation process according to the above patent is not selective. In U.S. Pat. No. 3,763,191, a process for the production of anthraquinone-α-sulphonic acids is suggested, especially anthraquinone-1-sulphonic acid by the sulphonation of anthraquinones in the presence of catalysts in solvents, the catalysts being metals of the 1st or 8th subsidiary group of the periodic system or compounds containing such metals. This process provides a high degree of selectivity for anthraquinone-1-sulphonic acid.

SUMMARY OF THE INVENTION

The present invention provides a process for the production of anthraquinone-1-sulphonic acid by sulphonating anthraquinone in the presence of palladium catalyst, and is characterized in that before sulphonation, palladium is mixed with nitric acid or other mineral acids containing nitric acid, and then the acid is removed from the treated palladium by a suitable method, preferably that which causes the treated palladium to be free from nitric acid. While it is taught in the above U.S. Patent that higher yields of anthraquinone-1-sulphonic acid are obtained when palladium or compounds containing palladium are used as catalysts, according to the present invention, it is found that the process employing nitric acid-treated palladium as described gives a yield of anthraquinone-1-sulphonic acid higher than that employing untreated palladium and higher as well than that utilizing palladium nitrate only or a combination of palladium and nitric acid, or a combination of palladium and palladium nitrate. The palladium after being treated with nitric acid increases effectively the yield of the anthraquinone-1-sulphonic acid, especially when a solvent containing a lower concentration of $SO_3$ is mixed with the nitric acid-treated palladium and then a sulphonating agent with a higher concentration of $SO_3$ is gradually added to the above mixture at a temperature of about 90–100 degs C. after the addition of the anthraquinone to that mixture at a temperature lower than 80 degs C. The amount of the nitric acid used may be 5–250 moles per mole of the palladium. The sulphonating agent used in the present invention may be any one of those used in known processes for sulphonating anthraquinones. Preferably, a sulphonating agent containing 1–10% by weight of $SO_3$ is first used and then the same sulphonating agent containing 50–65% by weight of $SO_3$ is finally added for sulphonation. The following examples are presented to illustrate the process of this invention.

FIG. 1 shows a diagram of the size distributions of the particle sizes of the palladium used in Examples 1, 2 and 3.

EXAMPLE 1.

(a) Treatment of palladium with nitric acid 0.14 gm of a technical grade palladium was mixed with 5 ml of 65% nitric acid. Nitrogen gas was passed through the above mixture at an elevated temperature of about 150–200 degs C. so as to carry away the nitric acid. The palladium has a purity of 99% and includes about 70% of particles smaller than 125 microns and about 30% of particles ranging from 125–1000 microns. The size distribution of the particles smaller than 125 microns is shown in FIG. 1.

(b) Alternative treatment of the palladium 0.14 gm of the above technical grade palladium was mixed with 10 ml of aqua regia. Then, the mixture was neutralized. The precipitated palladium was washed and dried.

(c) Sulphonation of anthraquinone in the presence of the nitric acid-treated palladium To a solution of 6 ml of 65% oleum in 14 ml of 95% sulphuric acid was added the nitric acid-treated palladium (Treatment (a)) at room temperature. Then, 20.8 gm of anthraquinone was added to the above mixture at a heated temperature of about 70 degs C. Finally, 10 ml of 65% oleum was added dropwise at 90 degs C. in one hour, and the mixture was agitated at this tempperature for another 3 hours. The reaction mixture contains the following mole percentages of components based on the moles of anthraquinone added.

| | |
|---|---|
| anthraquinone-1-sulphonic acid | 93.5% |
| anthraquinone-2-sulphonic acid | 0.6% |
| anthraquinone disulphonic acids | 1.9% |
| anthraquinone (unreacted) | 4.0% |

When the reaction mixture was diluted with water and filtered and the anthraquinone-1-sulphonic acid was salted out from the filtrate, 28.7 gm of sodium salt of the anthraquinone-1-sulphonic acid with 98% purity was obtained.

(d) When the above sulphonation process was carried out by varying the concentration of the oleum but the total moles of $SO_3$ used being unchanged, the following results are obtained.

| Oleum concentration | Anthraquinone (unreacted) | Anthraquinone-1-sulphonic acid, yield* |
|---|---|---|
| 40% | 2% | 42% |
| 30% | 8% | 47% |
| 25% | 10% | 62% |
| 20% | 14% | 56% |
| 15% | 25% | 50% |

*where the yield is based on anthraquinone added (e) When the above sulphonation process was carried out by varying the temperature and the reaction time, the following rersults are obtained.

| Temp. T1 °C. | Temp. T2 °C. | Reaction time hrs | Anthraquinone (unreacted) | Anthraquinone-1-sulponic acid, yield |
|---|---|---|---|---|
| 70. | 105 | 2 | | 72% |
| 70 | 100 | 2.5 | | 87% |
| 70 | 95 | 3 | 10% | 92% |

| Temp. T1 °C. | Temp. T2 °C. | Reaction time hrs | Anthraquinone (unreacted) | Anthraquinone-1-sulponic acid, yield |
|---|---|---|---|---|
| 70 | 85 | 6 | 35% | 60% |
| 70 | 75 | 8 | 84% | 15% |
| 60 | 90 | 3 | 5% | 75% |
| 60 | 90 | 3 | 5% | 92% | where T1 = Temperature at which anthraquinone was added
T2 = Reaction temperature

EXAMPLE 2

To a solution of 6 ml of 65% oleum in 14 ml of 95% sulphuric acid was added 1 gm of the nitric acid-treated palladium (Treatment (a)) at room temperature. Then, the solid palladium particles are separated from the resulting mixture by centrifugal separation. The size of the separated palladium particles was smaller than 125 microns and the particle size distribution thereof is shown in the following FIG. 1.

The sulphonation process (c) of Example 1 was carried out in the presence of 0.14 gm of the separated palladium particles smaller than 125 microns. The yield of the anthraquinone-1-sulphonic acid is 78%.

COMPARATIVE EXAMPLE 1

Sulphonation of anthraquinone in the presence of the untreated palladium

When the sulphonation process was carried out as described in Example 1 (c) but with the palladium being untreated, the reaction mixture contains the following mole percentages of components based on the moles of the anthraquinone added.

| | |
|---|---|
| anthraquinone-1-sulphonic acid | 67.8% |
| anthraquinone-2-sulphonic acid | 2.7% |
| anthraquinone disulphonic acid | 1.0% |
| anthraquinone (unreacted) | 28.5% |

When the temperature was varied, the results obtained are as follows:

| Reaction Temp. °C. | Anthraquinone (unreacted) | Anthraquinone-1-sulphuric acid, yield |
|---|---|---|
| 105 | 10.4% | 55% |
| 95 | 25% | 65.5% |
| 85 | 49.5% | 43.7% |

When the concentration of the oleum is varied, the results obtained are as follows:

| Oleum concentration | Anthraquinone (unreacted) | Anthraquinone-1-sulphonic acid, yield |
|---|---|---|
| 40% | 43.7% | 40.1% |
| 30% | 59.0% | 39.7% |
| 25% | 60% | 38.5% |
| 20% | 72% | 22% |
| 15% | 88.5% | 10.7% |

EXAMPLE 3

Sulphonation with a reagent grade palladium which has a purity of 99.98% and a particle size smaller than 125 microns, the particle size distribution being shown in FIG. 1

The above specified palladium was treated with nitric acid and the sulphonation process was carried out as described in Example 1 (c). The reaction mixture contains 94% by mole of anthraquinone-1-sulphonic acid based on the anthraquinone added.

COMPARATIVE EXAMPLE 2

When the sulphonation process of Example 3 was carried out but with the palladium being untreated, the reaction mixture contains 90% by mole of anthraquinone-1-sulphonic acid based on the anthraquinone added.

COMPARATIVE EXAMPLE 3

Sulphonation of anthraquinone in the presence of a mixture of palladium and palladium nitrate The sulphonating process was carried out described in Example 1 (c) but the nitric acid-treated palladium being replaced by a mixture of catalyst containing 0.07 gm of untreated palladium and 0.15 gm of palladium nitrate. The reaction produces anthraquinone-1-sulphonic acid in 58.5% yield, and the conversion is 70%.

COMPARATIVE EXAMPLE 4

Sulphonation of anthraquinone with palladium nitrate

When the sulphonation process was carried out as described in Example 1 (c) but the nitric acid treated palladium being replaced by 0.3 gm of palladium nitrate, the yield of the anthraquinone-1-sulphonic acid is about 44% and the conversion is 59%.

COMPARATIVE EXAMPLE 5

Sulphonation of anthraquinone in the presence of palladium and nitric acid

When the sulphonation process was carried out as described in Example 1 (c) but with the nitric acid-treated palladium being replaced by 0.14 gm of untreated palladium and 0.1 ml of 65% nitric acid, the yield of the anthraquinone-1-sulphonic acid is 42% and the unreacted anthraquinone is 9%.

What I claim is:

1. In a process for the production of anthraquinone-1-sulphonic acid by sulphonating anthraquinone with a sulphonating agent in the presence of palladium catalyst in a solvent, an improvement comprising: before sulphonation, mixing the palladium with nitric acid or mineral acids containing nitric acid at room temperature and then removing the acid from the treated palladium.

2. A process as claimed in claim 1, wherein the amount of the acid used contains 5–250 moles of nitric acid per mole of palladium.

3. A process as claimed in claim 1, wherein the nitric acid is removed by passing nitrogen gas through the mixture at a temperature of about 100–250 degs C.

4. A process as claimed in claim 1, wherein the acid is removed from the palladium by neutralization.

5. A process for the production of anthraquinone-1-sulphonic acid by sulphonating anthraquinone in the presence of palladium catalyst in a solvent comprising:
   (a) mixing the palladium with nitric acid and removing the nitric acid from the treated palladium;
   (b) mixing the nitric acid-treated palladium of step (a) with a sulphonating agent of a lower concentration of $SO_3$;
   (c) adding anthraquinone to the mixture of step (b) at an elevated temperature; and (d) adding gradually to the mixture of step (c) an additional amount of the same sulphonating agent as that of step (b) but with the $SO_3$ concentration being higher than that of step (b) at a further elevated temperature.

6. A process as claimed in claim 5, wherein the anthraquinone is added at a temperature lower than 80 degs C., and the sulphonating agent of step (d) is added at about 90–100 degs C.

7. A process as claimed in claim 6, wherein the anthraquinone is added at a temperature of about 70 degs C. and the sulphonating agent of step (d) is added at about 90 degs C.

8. A process as claimed in claim 6, wherein the sulphonating agent of step (b) consists of 1–10% by weight of $SO_3$, and the sulphonating agent of step (d) contains 50–65% by weight of $SO_3$.

9. A process as claimed in claim 8, wherein the sulphonating agent of step (b) contains 5% by weight of $SO_3$, and the sulphonating agent of step (d) contains 65% by weight of $SO_3$.

* * * * *